United States Patent [19]

Choong

[11] Patent Number: 5,290,766
[45] Date of Patent: Mar. 1, 1994

[54] CARDIOPLEGIC COMPOSITIONS

[75] Inventor: Yee S. Choong, Auckland, New Zealand

[73] Assignee: The National Heart Foundation of New Zealand, Auckland, New Zealand

[21] Appl. No.: 836,541

[22] Filed: Feb. 18, 1992

[30] Foreign Application Priority Data

Feb. 18, 1991 [NZ] New Zealand ............... 237139

[51] Int. Cl.$^5$ ............... A61K 31/70; A61K 31/715; A61K 33/14
[52] U.S. Cl. ............... 514/23; 514/832; 514/833; 435/1; 435/2; 128/897; 128/898; 604/49; 604/50; 604/51; 604/52; 424/679
[58] Field of Search ............... 514/832, 833, 23; 435/1, 2; 128/897, 898; 604/49-52; 424/679

[56] References Cited

U.S. PATENT DOCUMENTS

| | | | |
|---|---|---|---|
| 3,928,574 | 12/1975 | Phillips | 424/679 |
| 4,415,556 | 11/1983 | Bretschneider | 424/679 |
| 4,605,644 | 8/1986 | Foker | 514/45 |
| 4,719,201 | 1/1988 | Foker | 514/23 |
| 4,923,442 | 5/1990 | Segall et al. | 424/679 |
| 4,938,961 | 7/1990 | Collins et al. | 424/679 |
| 4,988,515 | 1/1991 | Buckberg | 424/682 |
| 5,082,831 | 1/1992 | Leaf et al. | 435/1 |

FOREIGN PATENT DOCUMENTS

| | | |
|---|---|---|
| 12272 | 6/1980 | European Pat. Off. |
| 2425264 | 12/1974 | Fed. Rep. of Germany |
| 3026368 | 2/1982 | Fed. Rep. of Germany |
| WO82/3773 | 11/1982 | World Int. Prop. O. |

OTHER PUBLICATIONS

"L-Aspartate Improves the Functional Recovery of Explanted Hearts Stores in St. Thomas' Hospital Cardioplegic Solution at 4° C.", *The Journal of Thoracic and Cardiovascular Surgery*, vol. 99, No. 3, pp. 510-517, Mar. 1990 by The C. V. Mosby Company Y. S. Choong, PhD, and J. B. Gavin, DDS, PhD.

*Primary Examiner*—Ronald W. Griffin
*Attorney, Agent, or Firm*—Young & Thompson

[57] ABSTRACT

An aqueous cardioplegic solution providing significantly improved cardiac function after a period of exposure to cardioplegia, contains NaCl in the range of 70-110 mM; KCl in the range of 10-16 mM; CaCl$_2$ in the range of 0.5-1.0 mM; MgCl$_2$ in the range of 8-16 mM; NaHCO$_3$ in the range of 10-20 mM; D-Glucose in the range of 5-15 mM; L-Aspartic acid in the range of 5-20 mM; and Lactobionic acid in the range of 0-15 mM.

3 Claims, 2 Drawing Sheets

CARDIOPLEGIC COMPOSITIONS

FIELD OF THE INVENTION

This invention relates to the use of artificial solutions (crystalloid cardioplegias) in which hearts may be flushed and/or stored in or undergo cardiac (open-heart) surgery.

BACKGROUND

There is a widely felt need for an improved or "ideal" cardioplegic solution, literally paralysing the heart (to stop electrical and mechanical activity) for prolonged and safe preservation of the myocardium (heart muscle). Such solutions are perfused through the vessels and chambers of the organ and, while maintaining viability, cause its intrinsic beating to cease. The effects of such solutions should be totally reversible, so that the heart resumes substantially normal functional activity once the cardioplegic solution has been replaced by blood. The provision of cardioplegic solutions is highly desirable during the procurement, transportation and storage of donor hearts for use in the increasingly frequently performed heart transplantation procedure and is even more desirable during open-heart surgery. Myocardial revascularisation (coronary artery surgery) and repairs (aortic and mitral valves replacement) is best achieved with a motionless and bloodless heart.

After cardio-pulmonary bypass is initiated the heart is infused with a cardioplegic solution. The presently available clinical cardioplegic solutions are considered to be imperfect as they provide reversible myocardial protection after hypothermic cardioplegic "arrest" for only a short period (up to 5 hours at 4° C. or less than 3 hours at 15°-20° C.). Even during that period the heart sustains some degree of ischemic injury which becomes progressively worse with time, resulting in significant deterioration of myocardial function on reperfusion which exacerbates the problems of postoperative recovery. The heart does not regain the efficiency it had before the bypassing procedure.

PRIOR ART

Attempts have been made to use several types of anti-freeze solution but this has not proved to be successful with larger organs such as the human heart.

A more successful composition is known as the St. Thomas' Hospital solution No. 2 which is an aqueous salt solution containing NaCl; KCl; $MgCl_2$; $CaCl_2$; and $NaHCO_3$.

Currently, the St. Thomas' Hospital No. 2 cardioplegic solution is commercially available as "PLEGISOL", (Abbott Laboratories, North Chicago, Ill., USA), yet it cannot be relied on to preserve the viability of hearts for periods beyond 4 to 5 hours at 4° C.

The inventor has discovered that the inclusion of L-aspartate (20 mM/liter) in a cardioplegic solution improved the viability of stored hearts as shown by the capability of the hearts to recover good pump function on reimplantation. This is described in:

Choong YS, Gavin JB,

L-Aspartate improves the functional recovery of explanted hearts stored in St. Thomas' Hospital cardioplegic solution at 4° C.

J Thorac Cardiovasc Surg 1990; 99: 510-517.

However, there is a need for an improved cardioplegic solution allowing for an even better recovery of pump function of hearts on reimplantation.

OBJECT

It is an object of the invention to provide an improved solution for cardioplegia or at least to provide the public with a choice in selection of solutions.

SUMMARY OF THE INVENTION

In one aspect the invention provides a cardioplegic solution including an amino acid, and/or a precursor or metabolic product thereof, together with glucose and alkali metal salts.

In another aspect the invention provides a premix for a cardioplegic solution including an amino acid, and/or a precursor or metabolic product thereof, together with glucose and alkali metal salts.

Preferably the premix includes one or more sterile packets containing the ingredients and/or at least one container of sterile fluid.

Preferably the invention also includes lactobionic acid.

In another aspect the invention provides a cardioplegic solution comprising inorganic cations including potassium, calcium, magnesium, and sodium, and anions including chloride and bicarbonate. Preferably the amino acid is aspartic acid, the asparatate anion, or a precursor, or metabolic product of it.

In another aspect the invention provides a cardioplegic solution comprising NaCl in the range of 70-110 mM, KCl in the range of 10-16 mM, $CaCl_2$ in the range of 0.5-1.0 mM, $MgCl_2$ in the range of 8-16 mM, $NaHCO_3$ in the range of 10-20 mM, D-Glucose in the range of 5-15 mM, L-Aspartic acid in the range of 5-20 mM, and Lactobionic acid in the range of 0-15 mM.

In a further aspect the invention provides a cardioplegic solution comprising (1) NaCl, 100 mM, (2) KCl, 10 mM, (3) $CaCl_2$, 0.8 mM, (4) $MgCl_2$, 10 mM, (5) $NaHCO_3$, 10 mM, (6) D-Glucose, 10 mM, (7) L-Aspartic acid, 10 mM, and (8) Lactobionic acid, 5 mM.

In another aspect the invention provides a method for creating a cardioplegic solution, in which the constituents are prepared and mixed in a prescribed manner.

Preferably this manner of preparation consists of first preparing the required amounts of aspartic and lactobionic acids by dissolving each in a small amount of distilled water and neutralizing to pH 7.5 with sodium hydroxide. This normally requires an equimolar amount of sodium hydroxide. The solution is then made by adding the various constituents in the sequence as listed here (1) NaCl, (2) KCl, (3) $CaCl_2$, (4) $MgCl_2$, (5) $NaHCO_3$, (6) D-Glucose, (7) L-Aspartic acid, and (8) Lactobionic acid to a large volume (70% total) of distilled water, mixing the solution after each addition. The cardioplegia is then bubbled with a gaseous mixture of 95% oxygen: 5% carbon dioxide for 5 minutes. The solution is then passed through a 0.2 μm cardioplegic filter and is ready for use.

PREFERRED EMBODIMENTS

These details are given by way of example and are in no way intended to be limiting. Variations on the preferred embodiment may be perceived by the reader skilled in the art, but will lie within the spirit or scope of the invention as given here. This particular preferred embodiment is identified herein as "MBS".

These and other aspects of this invention, which should be considered in all its novel aspects, will become apparent from the following description, which is given by way of example only, with reference to the accompanying drawings.

FIGURES

Table 1 defines one preferred formulation of cardioplegic solution, according to the invention.

TABLE 1

| Compound | Concentration |
| --- | --- |
| 1) NaCl | 100 mM |
| 2) KCl | 10 mM |
| 3) CaCl$_2$ | 0.8 mM |
| 4) MgCl$_2$ | 10 mM |
| 5) NaHCO$_3$ | 10 mM |
| 6) D-Glucose | 10 mM |
| 7) L-Aspartic acid | 10 mM |
| 8) Lactobionic acid | 5 mM |

Procedure for reconstituting this formulation "MBS" ready for use.

The required amounts of aspartic and lactobionic acids are each dissolved in a small amount of distilled water and neutralised to pH 7.5 with sodium hydroxide. This normally requires an equimolar amount of sodium hydroxide. The solution is then made by adding the various constituents in the sequence as listed in Table 1 to a large volume (70% total) of distilled water, mixing after each addition. The cardioplegia is then bubbled with a gaseous mixture of 95% oxygen: 5% carbon dioxide for 5 minutes. The solution is then passed through a 0.2 μm cardioplegic filter and is ready for use.

EXPERIMENTAL EVIDENCE—in vitro RESULTS

Figure 1:
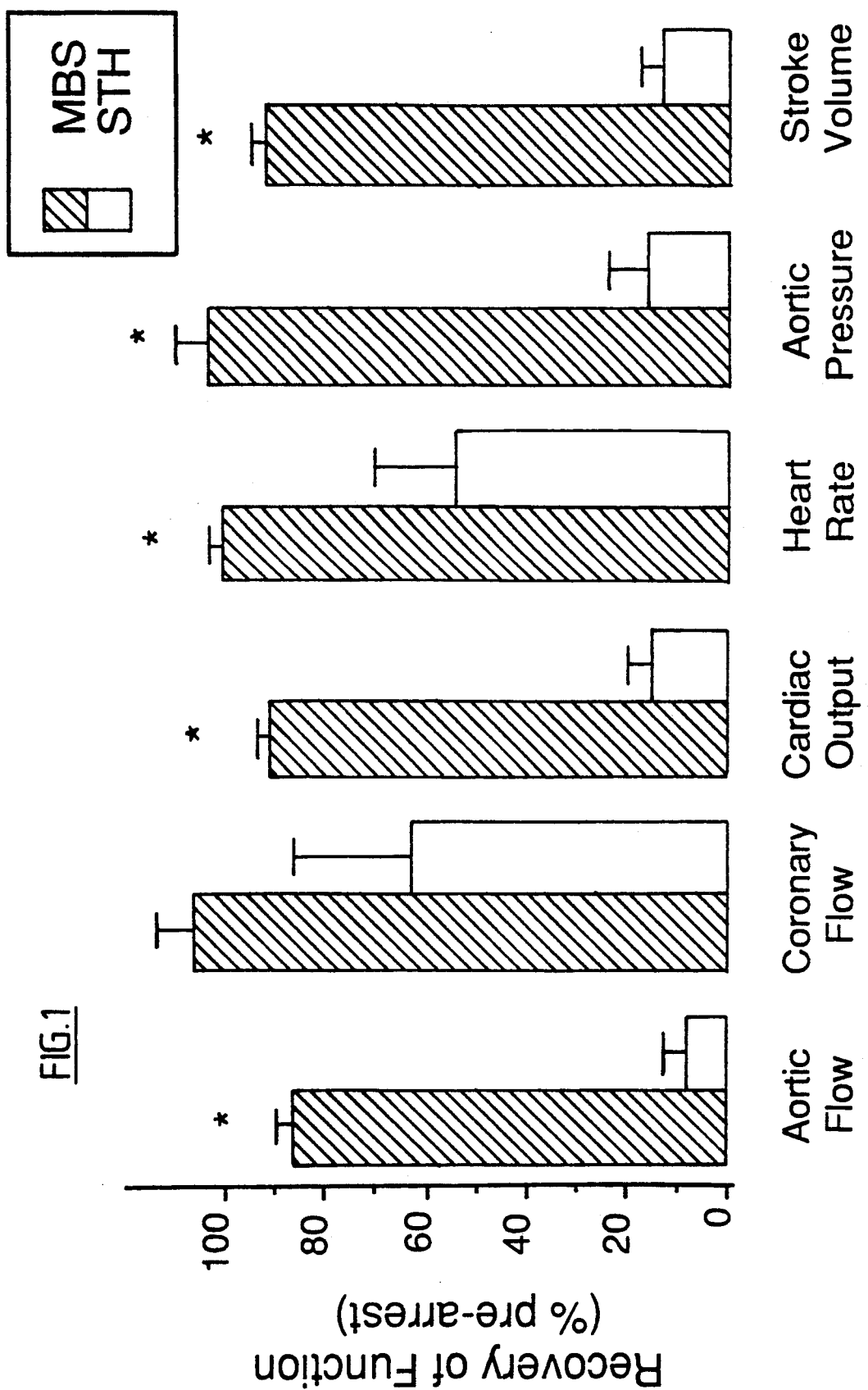
FIG. 1 is a bar-graph showing cardiac functions which compares the effects on isolated rat hearts of exposure to STH or a preferred embodiment of the invention, "MBS".

Refer to FIG. 1.

The inventor investigated the efficacy of this novel cardioplegia (identified within experiments as MBS, formulated as in Table 1) compared to the clinical St Thomas' Hospital No. 2 solution (STH).

Explanted rat hearts (9 per group) were arrested with either MBS or STH, both at 4 degrees Celsius, and subjected to ischemic injury for 6 hours at 20° C. During this long cross-clamping time the hearts were also repeatedly flushed (2 minute dose per 40 minute interval) simulating the event in human heart surgery. As shown in FIG. 1, only the MBS-treated hearts recovered virtually 100% cardiac pump function indicating very good protection of the cardiac muscle. In contrast, all the STH-treated hearts regained very poor cardiac function (0–55%) of the pre-arrest control values. This was—on statistical analysis—a highly significant result.

The "T"-shaped marks indicating the standard error (S.E.) are worthy of comment. When "STH" is used, some hearts are practically moribund and cause the S.E. to be larger; whereas with the "MBS" composition made according to this invention, hearts perform more consistently after exposure to cardioplegia.

Figure 2:
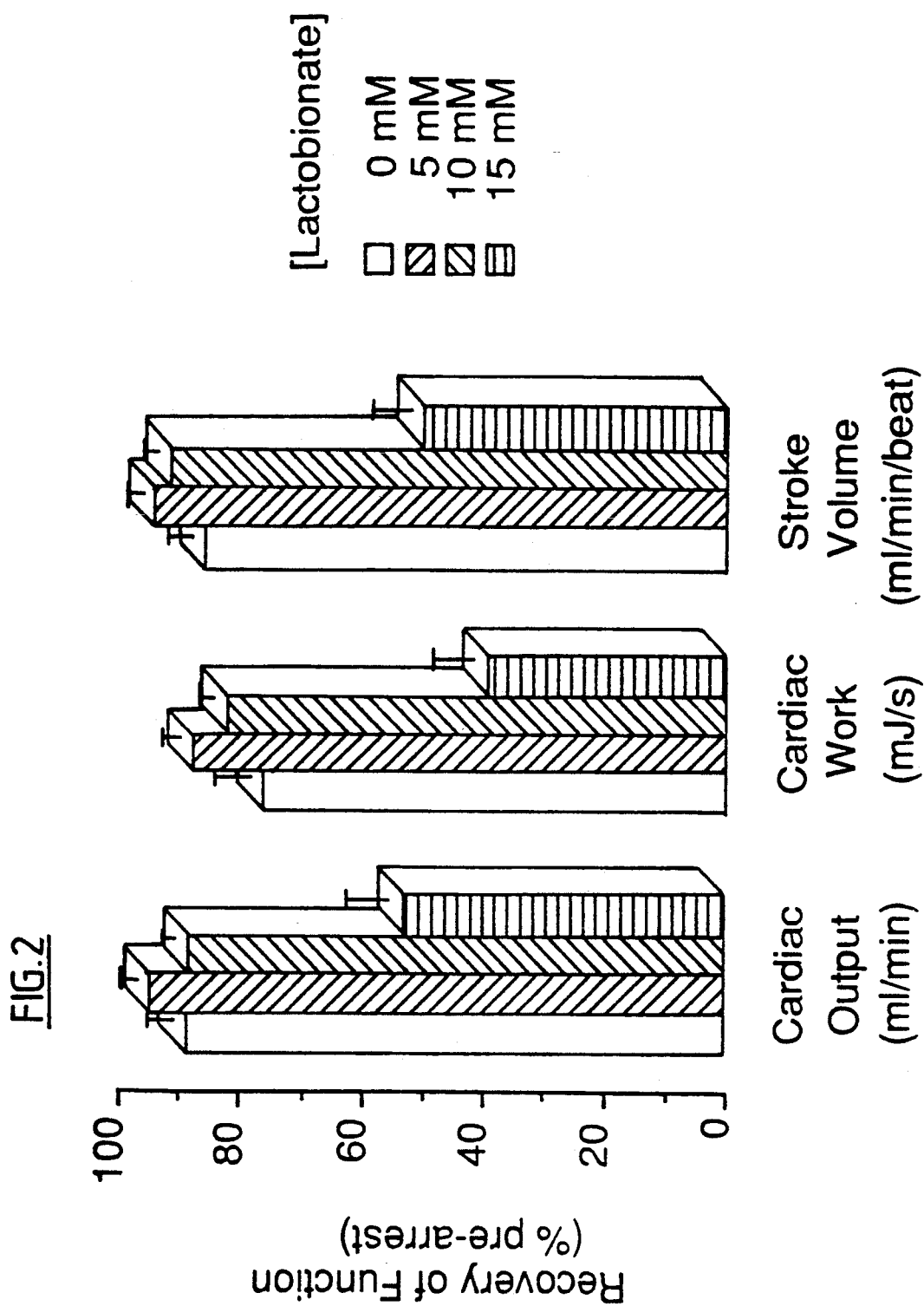
FIG. 2 is a bar-graph which demonstrates the existence of an optimal concentration of lactobionate in MBS on ischaemic arrested hearts.

FIG. 2 illustrates the results of a set of experiments designed to indicate the optimal concentration of lactobionate in the MPS solution. The arrested hearts had been stored in the solution under test for 6 hours at 20 degrees C. before restoration and testing. The results indicate that 5 mM or perhaps 6 or 7 mM of lactobionate is the optimal concentration of this material. Again, the standard error symbols indicate a consistent response. The numbers of hearts used are: for the 0 mM solution, n=8; for the 5 mM solution, n=10; for the 10 mM solution, n=9, and for the 15 mM solution, n=9.

ADVANTAGES OF PREFERRED EMBODIMENT

Our reasons for providing embodiments of the invention in accordance with Tables 1 or 2 are that the following materials benefit the ischemic heart by providing:

Aspartate—metabolic intermediate of the Tricarboxylic Acid Cycle in the mitochondria and NADH/NAD redox potential regulation.

Glucose—metabolic substrate in the Glycolytic Pathway.

Lactobionate—oncotic agent to prevent excessive loss of extracellular water.

Potassium chloride—allows the rapid diastolic arrest of the heart.

Sodium chloride—maintains extracellular fluid concentration.

Magnesium chloride—minimises differences in the intracellular fluid concentration.

Calcium chloride—prevents the efflux of Ca$^{++}$ in mitochondria and contractile fibers.

POSSIBLE VARIATIONS OF THE PREFERRED EMBODIMENT

This table gives preferred and illustrative ranges for variations of the composition of our cardioplegic solution. It should be noted that interactions between components (such as in relation to oncotic pressure) mean that alterations are preferably made with care, and with due consideration of other constituents.

TABLE 2

| | Range |
| --- | --- |
| NaCl | 70–110 mM |
| KCl | 10–16 mM |
| CaCl$_2$ | 0.5–1.0 mM |
| MgCl$_2$ | 8–16 mM |
| NaHCO$_3$ | 10–20 mM |
| D-Glucose | 5–15 mM |
| L-Aspartic acid | 5–20 mM |
| Lactobionic acid | 0–15 mM |

Finally it will be appreciated that various other alterations or modifications may be made to the foregoing without departing from the scope of this invention as set forth in the following claims.

I claim:

1. A sterile aqueous cardioplegic solution comprising NaCl in the range of 70–110 mM; KCl in the range of 10–16 mM; CaCl$_2$ in the range of 0.5–1.0 mM; MgCl$_2$ in the range of 8–16 mM; NaHCO$_3$ in the range of 10–20 mM; D-Glucose in the range of 5–15 mM; L-Aspartic acid in the range of 5–20 mM; and Lactobionic acid in the range of 0–15 mM.

2. A cardioplegic solution as claimed in claim 1, having a pH of about 7.5 and containing about 100 mM of NaCl; about 10 mM of KCl; about 0.8 mM of CaCl$_2$; about 10 mM of MgCl$_2$; about 10 mM of NaHCO$_3$;

about 10 mM of D-Glucose; about 10 mM of L-Aspartic Acid; and about 5 mM of Lactobionic Acid.

3. A method for creating a cardioplegic solution, in which the constituents are prepared and mixed as follows:
   (a) the required amounts of aspartic and lactobionic acids are each dissolved in a small amount of distilled water and neutralized to pH 7.5;
   (b) the cardioplegic solution is made by adding the various constituents in the sequence as listed here (1) NaCl, (2) KCl, (3) CaCl$_2$, (4) MgCl$_2$, (5) NaHCO$_3$, (6) D-Glucose, (7) L-Aspartic acid, and (8) Lactobionic acid to a large volume (about 70% total) of distilled water, mixing the solution after each addition;
   (c) the balance of distilled water is added to the cardioplegic solution;
   (d) the cardioplegic solution is bubbled with a gaseous mixture of 95% oxygen:5% carbon dioxide for about 5 minutes; and
   (e) the cardioplegic solution is passed through a cardioplegic filter before use.

* * * * *